United States Patent [19]

Sogo

[11] 4,107,994
[45] Aug. 22, 1978

[54] LEVEL DETECTOR

[75] Inventor: Masaaki Sogo, Kobe, Japan

[73] Assignee: Sanko Air Plant Ltd., Osaka, Japan

[21] Appl. No.: 704,807

[22] Filed: Jul. 13, 1976

[30] Foreign Application Priority Data

Jul. 21, 1975 [JP] Japan .................................. 50-88340

[51] Int. Cl.² ............................................ G01F 23/26
[52] U.S. Cl. ................................... 73/290 V; 340/615
[58] Field of Search .......... 73/290 V; 340/236, 244 R; 259/DIG. 44

[56] References Cited

U.S. PATENT DOCUMENTS

| 2,668,365 | 2/1954 | Hogin ................ | 73/290 V |
|---|---|---|---|
| 3,019,650 | 2/1962 | Worswick ............. | 73/290 V |
| 3,058,014 | 10/1962 | Camp ................ | 259/DIG. 44 |
| 3,198,489 | 8/1965 | Finch ................ | 259/DIG. 44 |
| 3,220,258 | 11/1965 | Rod .................. | 73/290 V |
| 3,256,738 | 6/1966 | Di Giacomo et al. ... | 73/290 V |
| 3,287,720 | 11/1966 | Chambers et al. ...... | 340/244 R |
| 3,730,489 | 5/1973 | Morita ............... | 259/DIG. 44 |
| 3,985,030 | 10/1976 | Charlton ............. | 73/290 V |

FOREIGN PATENT DOCUMENTS

| 216,053 | 3/1957 | Australia .............. | 73/290 V |
|---|---|---|---|
| 839,092 | 6/1960 | United Kingdom ....... | 73/290 V |

OTHER PUBLICATIONS

Publ. "Mechanical & Electric Sensors Monitor Level & Flow" by Design Engineering (Mar. 1971) Mater & Compen (G.B.) pp. 59–63.

*Primary Examiner*—Daniel M. Yasich
*Attorney, Agent, or Firm*—Murray & Whisenhunt

[57] ABSTRACT

A level detector is disclosed for detection of whether or not the level of the contents in a container, such as powder, grains, or liquid, attains a predetermined one. Said detector includes a coil and a vibrating plate consisting of a magnetic material or having a magnetic portion which plate is disposed in such a manner that the surface of said vibrating plate is nearly flush with that of the inner wall surface of said container. Said vibrating plate is vibrated by a coil disposed oppositely to said vibration plate and a drive unit to supply a pulse current to said coil. A mechanical vibrating-electric converter which is mounted on said vibrating plate converts the vibrations of said plate caused by said pulse currents into electric signals, and a sensor detects any differences in the amplitude between said electric signals detected when said contents are in contact with said vibrating plate or when said contents are not in contact with said vibrating plate.

7 Claims, 11 Drawing Figures

P

S $S_1$ $S_s$

LEVEL DETECTOR

BACKGROUND OF THE INVENTION

The present invention generally relates to a level detector, and more particularly, to a level detector suitable for detection of whether or not the level of the contents, such as powder, grains or liquid, in a silo or hopper attains a predetermined one.

Generally, a level detector is provided to a container such as a tank, hopper or silo to determine the level of the contents, such as powder, grains or liquid, in the container. For example, two level detectors are provided at the upper and lower parts of a hopper, respectively, to detect whether or not the level of pellets of synthetic resin materials is at a predetermined one, in order to maintain a correct supply of pellets in the hopper.

Conventionally, the torque-motor type, capacitive type, phototube type, ultrasonic type and tuning-fork type level detector have been used for detection of the levels of such materials.

In the case of a torque-motor type level detector, a vane made to turn by a small torque motor is provided in a container. When the container is empty, the vane is not loaded. When contents are placed in the container, the vane is then loaded to actuate the limit switch. In this type of a level detector, the torque motor is made to turn continuously. Accordingly, the motor is easily wasted and the service life of the motor is shortened. Further, the vane projecting inwardly of the container disturbs the flow of the contents in the container, and the vane itself is likely to be damaged by the flow of the contents in the container.

In a capacitive-type level detector, the level of any object is detected according to the difference in capacitance between the tip and base of a projecting bar provided inside the container, which capacitance depends on the existence of such an object. However, when the detecting bar is contaminated, its sensitivity varies, causing the detector to fail. Further, when ambient conditions, for example, the humidity, change, the capacitance between said tip and base also changes. For this reason, it is difficult to present said detector at a desirable level. The detection bar projecting inside the container is pressed by the flow of the contents such as powder, grains or liquid, and is thus easily broken.

With a phototube type level detector, the level of the contents, such as of powder, grains or liquid, is detected by an arrangement whereby a light beam from a projector is interrupted by objects existing in the container. However, such level detection is impossible for any contents, which are transparent. Further, the beam receiver window of the phototube is easily dimmed by the contents, resulting in failures of said phototube type detector.

In the case of a tuning-fork type level detector, a projecting tuning fork activated by an exciter is provided inside the container. The level is detected based on the principle in which the oscillating state of the tuning fork varies depending on the varying volume of the contents in the container. However, there is a danger for the projecting tuning fork to be broken under the flow pressure.

Finally, the ultrasonic level detector detects the level of the contents in a container based on the reflection time of an ultrasonic wave between the top end of the container and the top surface of the contents contained therein. Disadvantageously such ultrasonic type detector is very expensive.

SUMMARY OF THE INVENTION

Provided in this invention is a level detector for detecting the level of the contents, such as powder, grains or liquid, in the container, which detector is very durable without having any danger of being damaged by the flow pressure, is inexpensive in cost, and can surely detect the existence of said contents when said contents have reached a predetermined level inside the container.

A vibrating plate consisting of a magnetic material or having a magnetic material portion is disposed as nearly flush with the inner wall surface of the container so that the plate may be in contact with said contents. The vibrating plate is vibrated by a coil disposed oppositely to the vibrating plate and a drive unit to supply a pulse current to the coil. A mechanical vibrating-electric converter which is mounted on the vibrating plate converts the vibrations of the plate caused by the pulse current into electric signals, from which signals a sensor detects any differences in the amplitude between said electric signals detected when said contents are in contact with the vibrating plate or when said contents are not in contact with the vibrating plate.

The vibrating plate is disposed as generally flush with the wall of the container and does not protrude inwardly of the container wall. Thus, there is no danger for the plate to be damaged by the flow pressure of the contents. Further, the plate could not be damaged by the lateral pressure since the pressure is extremely low if the hopper is full of the contents. Because the vibrating plate is always forcibly vibrated, it is difficult for the contents to be deposited on said plate. Thus, the operation of the level detection according to the present invention rarely exhibits faults caused by adherence of such contents to the level detector. Accordingly, the level detector of the present invention is inexpensive in manufacturing cost, long in service life and high in reliability.

For a better understanding of the present invention, together with other and further objects thereof, reference is made to the following description disclosed in connection with the accompanying drawings, its scope will be pointed out in the appended claims.

DETAILED DESCRIPTION OF THE INVENTION

Figure 1:
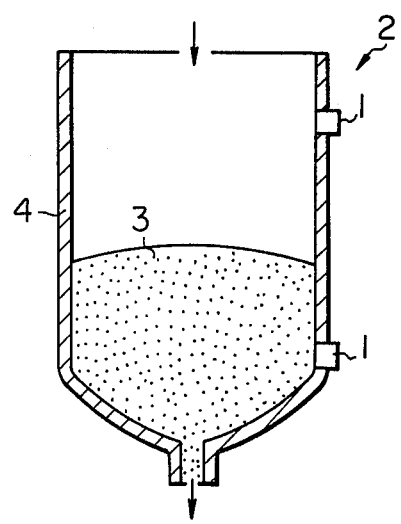
FIG. 1 is a schematic sectional view of a hopper provided with a level detector according to the present invention.

Referring now to FIG. 1, the level detectors (1, 1) according to the present invention are provided at the upper and lower portions of the wall 4 of a hopper 2. The level detectors (1, 1) detect the level of grains 3 such as pellets inside the hopper to prevent the hopper 2 from being excessively or insufficiently supplied or charged with the grains 3.

Figure 2:
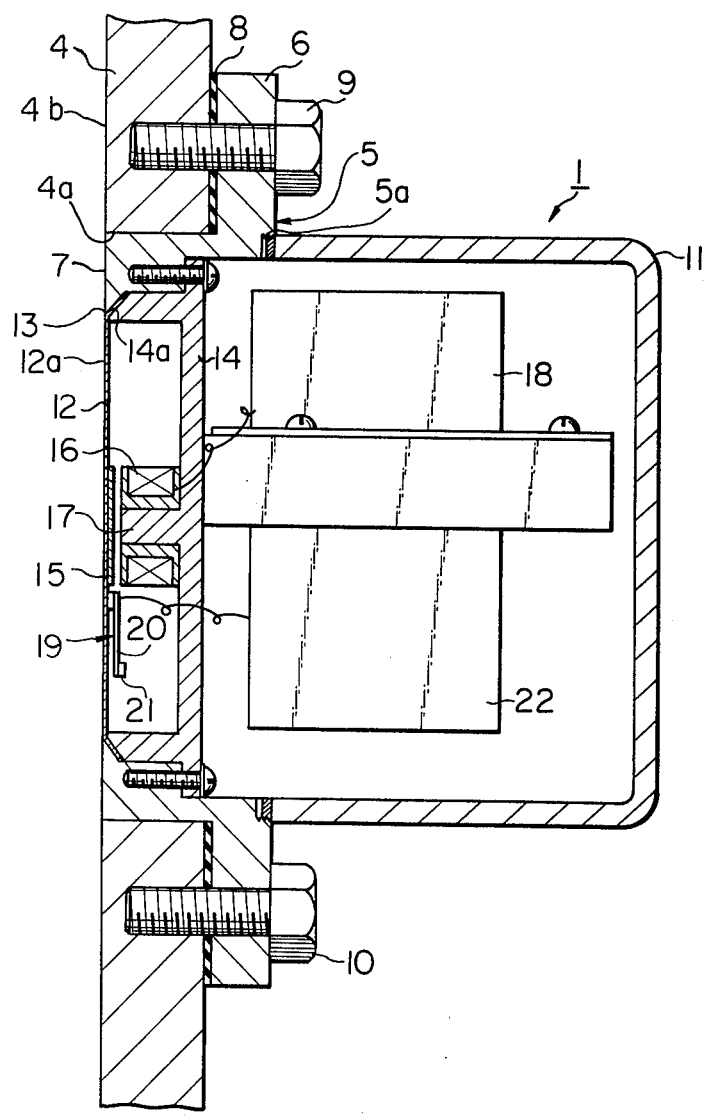
FIG. 2 is a sectional view on a larger scale of the level detector in FIG. 1.

FIG. 2 shows one of the level detectors on a larger scale. The level detector 1 comprises a cylindrical mounting frame 5 which has an outward flange 6 formed integrally therewith. The mounting frame 5 is fitted in the opening 4a which is provided in the wall 4 of the hopper 2. Further, in order that the end face 7 of the frame 5 be in the same plane as the inner face of the wall 4, the axial length of the cylindrical portion of the frame 5 is approximately equal to the thickness of the wall 4. The frame 5 is securely mounted through an annular gasket 8 to the wall 4 by means of an outward flange 6 and screws 9, 10. Thus, if the contents inside the hopper is liquid, there is no possibility of a leakage occurring through the gap between the opening 4a and the frame 5. At the other end of the frame 5, a threaded portion 5a is formed, and casing 11 is screwed into the threaded portion 5a.

In the proximity of the end face 7, is provided a vibrating plate 12 which has a magnetic portion and is disposed in such a manner that the surface 12a of the vibrating plate 12 is nearly flush with that of the inner wall surface 4b of the wall 4 of the hopper 2 so that the plate 12 may be in contact with the grains 3 in the hopper 2. According to the illustrated embodiment, the vibrating plate 12 is supported as clipped onto the outer periphery by an inward flange 13 provided on the inner periphery of the opening, and an outer end face 14a of a cap-shaped retainer 14 is secured onto the frame 5. The vibrating plate 12 has at least a magnetic portion so that the plate may be vibrated under the effect of the magnetic force of the coil which will be described later. In the case of the embodiment illustrated in the Figures, the vibrating plate 12 is made of stainless steel to prevent it from being corroded by the material received in the hopper. Therefore, a piece of iron 15 is secured by an appropriate means such as by welding the piece of iron to the vibrating plate 12 nearly at the center of the plate 12 inside the frame 5. As seen in the foregoing, the vibrating plate 12 may of course be made of a magnetic material (e.g. iron).

To make the vibrating plate 12 vibrate electromagnetically, a coil 16 is provided to the column 17 located at the center of the retainer 14 in a manner wherein the coil 16 is disposed oppositely to the vibrating platr 12, in particular, to the iron piece 15 forming a magnetic portion of the plate. Said coil 16 is driven by the pulse current from a drive unit 18 accomodated in the casing 11, to intermittently attract the vibrating plate 12, thus making the plate 12 vibrate. In the meanwhile, the vibrating plate 12 is provided with a mechanical vibrating-electric converter unit 19 (will be referred to simply as "converter") to transform into an electric signal the vibrating of the vibrating plate 12 caused by the pulse current from the drive unit 18. The converter 19 has a piezo-electric element 20 attached at one end to the vibrating plate 12 by means of a binding screw or other appropriate means, the other end being provided with a weight 21. Said piezo-electric element 20 is disposed generally in parallel to the vibrating plate 12. Thus, when the vibrating plate 12 is made to vibrate, the piezo-electric element 20 is subjected to a mechanical distortion under the inertial effect of the weight 21. A piezo-electric signal occurs across the electrodes of the element 20 (not shown) corresponding to the vibration. In this way, the mechanical vibration is converted into an electric signal. Since the converter 19 is secured at only one end, the piezo-electric element 20 moves along with the weight 21 when a large vibration occurs. Thus, the converter 19 may not be broken by a possible large vibration. The converter 19 may otherwise be constructed. Namely, a coil may be so arranged to move through a constant magnetic field when the vibrating plate 12 is oscillated. Or, such an arrangement may be made whereby a permanent magnet is displaced in a fixed coil. As seen in the foregoing, the vibrating plate 12 energized by the coil 16 vibrates in a different manner, depending on either of the cases where the vibrating plate 12 is not in contact with the grains 3 because the level of the grains 3 is too low, or where the plate 12 is always in contact with the grains 3 because the level of said grains 3 is high. More particularly, in the former case, the amplitude of the vibration of the plate 12 energized by the coil 16 is large and lasts for a relatively long time, while in the latter case, the amplitude of the vibration is small and lasts only for a short time. Consequently, the electric signal from the converter 19 corresponds to such a vibration and is supplied to the sensor 22 which detects any differences in the amplitude between the electric signals delivered when the grains 3 are in contact with the vibrating plate 12 or when the grains 3 are not in contact with the vibrating plate 12.

Figure 3:
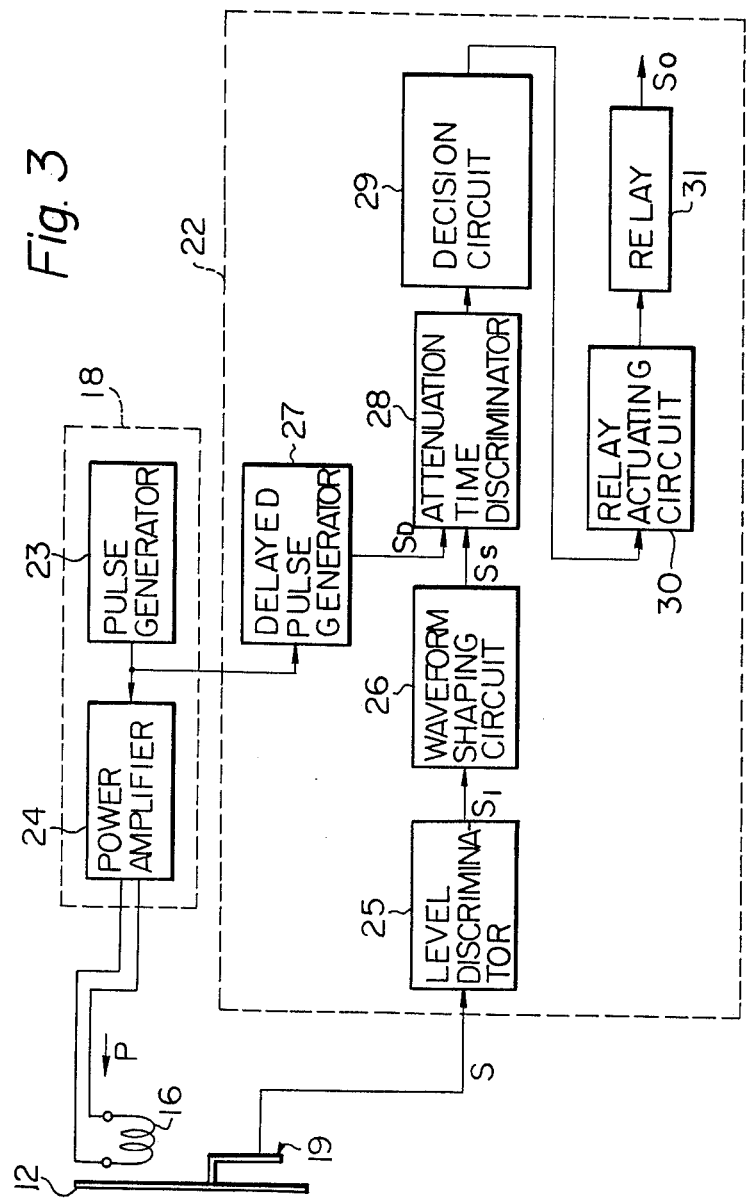
FIG. 3 is a block diagram of the electric circuitry of the level detector.
Figure 5A:
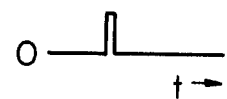
FIGS. 5A through 5D show the waveforms of signals passing through the electric circuitry in FIG. 3 when the grains are in contact with the vibrating plate.

FIG. 3 is a block diagram of a drive unit 18 and a sensor 22. The drive unit comprises a pulse generator 23 when generates a pulse signal of a predetermined time duration and having a predetermined number of pulses, and a power amplifier 24 which amplifies the pulse signal from the pulse generator 23 to a given magnitude for supplying a pulse current P to the coil 16. As the pulse generator, for example, a well known blocking oscillator can be used. The magnetic attraction created by the pulse current P will force the vibration plate 12 to vibrate intermittently as mentioned previously. Such vibration is converted into an electric signal S by the converter 19 due to the mechanical distortion being converted into a piezo-electric signal, which is supplied to the sensor 22. The sensor 22 comprises a level discriminator 25 which discriminates the electric signal S in such a way that only an electric signal S of a level higher than the predetermined discriminating level $V_D$ is permitted to pass. The level discriminator 25 can be formed by using a transistor amplifier in which a predetermined voltage value is applied to an input electrode (e.g., a base electrode of an input transistor of an amplifier) as a bias voltage in order to relatively shift the level of the signal S to the transistor by the value $V_D$. Such a circuit technique is well known to the prior art.

Figure 4A:
FIGS. 4A through 4D show the waveforms of signals passing through the electric circuitry in FIG. 3 when the grains are not in contact with the vibrating plate.
Figure 4B:
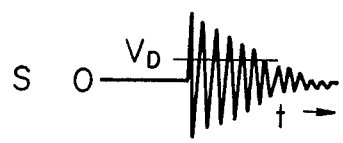
Figure 5B:
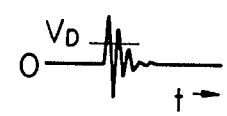
Figure 4C:
Figure 5C:
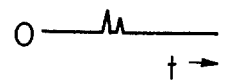
Figure 4D:
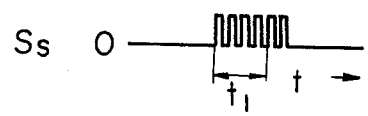
Figure 5D:
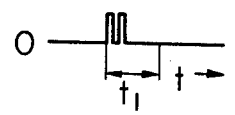

Instead of the circuit construction described above, a Schmidt trigger circuit may also be used as a level discriminator 25. In the case of using the Schmidt trigger circuit, the Schmidt trigger circuit operates in such a way that the output signal of the Schmidt trigger circuit becomes a high level only when the value of the signal A is higher than the predetermined level value $V_D$ (shown in FIG. 4b). As a result, the waveform of the output from the Schmidt trigger circuit is the same waveform as the waveform shown in FIG. 4d. Therefore, when the Schmidt trigger circuit is used as the level discriminator 25, the waveform shaping circuit may be omitted. The output signal S1 from the level discriminator 25 is applied to the waveform shaping circuit 26 from which signal $S_1$ is extracted as square-wave signal $S_S$. The waveform shaping circuit 26 can be formed by using a transistor which is operated at both saturation and cut-off conditions according to the output signal from the level discriminator. Such a circuit is widely used as a waveform shaping circuit. This square-wave signal $S_S$ is applied to an input terminal of the attenuation time discriminator 28. To another input terminal of the attenuation time discriminator 28 is applied the pulse signal $S_D$ delayed by a predetermined time of $t_1$ generated by the delayed pulse generator 27 being supplied with said pulse signal from the pulse generator 23. As the delayed pulse generator 27, for example, a delay line of a D-type flip-flop can be used, and the pulse width of the delayed pulse is determined in such a way that the pulse width is longer than one period of the signal S. The attenuation time discriminator 28 discriminates whether or not the square-wave signal $S_S$ lasts at a time determined by the delay time $t_1$. The discriminated result is delivered as logic "1" or "0" from the discriminator 28, for example. The attenuation time discriminator 28 can be constructed by use of an AND gate and a hold circuit. Signals $S_S$ and $S_D$ are applied to each of the input terminals of the AND gate, respectively. Therefore, if the signal $S_S$ still exists after time $t_1$, the output of the gate becomes a high level at the time when the level of the signal $S_S$ is a high level and the level of the signal $S_D$ is a high level. Thus, when the output of the AND gate becomes a high level, the condition of the high level of the AND gate is maintained by the hold circuit. The output from the hold circuit is delivered as the output of the attenuation time discriminator 28. In this case, it is necessary to reset the hold circuit in synchronization with the generation of the pulse current P so as to prepare the next detecting operation. This reset operation can be performed by use of the pulse current P, and this arrangement is very well known. When the signal $S_S$ vanishes before the time $t_1$, since the output of the AND gate never becomes a high level at the time when the pulse $S_D$ is supplied to the AND gate, the condition of the output of the hold circuit remains at a low level. Thus, if a signal higher than the predetermined level lasts for more than a set time $t_1$ (namely, when the level of grains 3 has not yet reached the level of the vibrating plate 12), a signal "0" is delivered. On the contrary, if a signal higher than the predetermined level does not last for more than a set time $t_1$ (that is to say, when the level of grains 3 (FIG. 1) is higher than that of the vibrating plate 12), a signal "1" is delivered. These outputs are judged by the decision circuit 29. The decision circuit 29 is arranged to operate the relay actuating circuit 30 in response to the condition of the output of the attenuation time discriminator 28 with high reliability.

That is, in the embodiment described above, it is arranged that the level of grains may be known from the attenuation time of the electric signal S derived from the converter 40. Since the attenuation time is variable when the pellets charged into the hopper collide with the vibrating plate, however, only one decision will provide a result which is not reliable. To eliminate such disadvantages, an arrangement may be made whereby an output signal $S_O$ is delivered when identical decision results are provided successively at a predetermined number of times by repeating the previously mentioned measurement several times. A counter which counts the output signal from the attenuation time discriminator 28 applied to the decision circuit in the form of the pulse signal and is reset after a predetermined period may be used as the decision circuit. According to such circuit construction, only when the number of the pulse signals from the attenuation time discriminator 28 exceeds a predetermined number during the foregoing described predetermined period, can the output signal of the decision circuit 29 be delivered from a predetermined output of the counter. However, in order to simplify the construction of the device, the decision circuit can be omitted.

The relay actuating circuit 30 is an amplifier for amplifying the output signal from the decision circuit 29 to a level high enough to actuate a relay 31. In this embodiment, the relay actuating circuit 30 is arranged in such a way that, when the output signal of the decision circuit 29 is at a high level, the relay 31 is driven to deliver an output signal $S_P$ which will be transmitted to a controller (not shown).

FIGS. 4A through 4D and 5A through 5D illustrate the time-base relation between these signals.

Further, the level of pellets may be determined according to the electric signal S, based on the fact that the initial amplitude of vibration of the plate 18 is different, depending on either of the case where the level of pellets is higher or lower than that of the vibrating plate.

The above embodiment has been described with respect to the level detection of grains. However, the present invention is also applicable to the level detection of powder, liquid or a mixture of both.

What we claim is:

1. A level detector for use in detecting whether the level of contents in a container has reached a predetermined level, said detector comprising:
   coil means for producing an electromagnetic force;
   driving means for intermittently supplying pulse signals to said coil;
   vibrating plate means having a surface substantially flush with the surface of the inner wall of the container, said coil means in close proximity to said vibrating plate means so that said plate means is intermittently vibrated by said electromagnetic force, the vibrating condition of said plate means changing depending on whether or not said contents contact said plate means;
   mechanical vibrating-electric converter means for converting the vibrations of said plate means into an electric signal with changes on the attenuation time of the intermittent vibrations of said plate means, said converter means attached to said vibrating plate means having one end attached to said vibrating plate means and means secured to the other ends of the piezo-electric element to produce a distortion effect to said piezo-electric element under inertial influence of said means; and
   detecting means for detecting changes in said electric signal caused by changes in said attenuation time, to thereby determine if the level of the container contents has reached said predetermined level.

2. A level detector according to claim 1, wherein said vibrating plate means is made of a magnetic material.

3. A level detector according to claim 1, wherein said vibrating plate means has a magnetic material portion.

4. A level detector according to claim 1, wherein said detecting means comprises means for discriminating whether or not the level of the initial amplitude said electric signals is more than a predetermined level.

5. Detector of claim 1, wherein said detecting means includes attenuation time detecting means for detecting the attenuation time differences of said plate means.

6. A level detector according to claim 1, wherein said detecting means comprises level discriminator means for discriminating said electric signals to pass only that part of said electric signal of a level higher than a predetermined level, and attenuation time discriminator means for discriminating whether or not the signal from said level discriminator lasts for more than a predetermined time.

7. A level detector for use in detecting whether the level of contents in a container has reached a predetermined level, said detector comprising:

coil means for producing an electromagnetic force;

driving means for intermittently supplying pulse signals to said coil;

vibrating plate means having an interior surface substantially flush with the surface of the inner wall of the container, said coil means in close proximity to said vibrating plate means so that said plate means is intermittently vibrated by said electromagnetic force, the vibrating condition of said plate means changing depending on whether or not said container contents contact said plate means; and mechanical vibrating-electric converter means for converting the vibrations of said plate means into an electric signal, said converter means comprising a piezo-electric element secured at one end to the exterior side of the vibrating plate means and a weight secured to the other end of said piezo-electric element to produce a distortion effect to said piezo-electric element under the inertial influence of the weight; and detecting means for detecting changes in the said electric signal.

* * * * *